Oct. 20, 1931. O. A. MÜLLER Plant Pat. 3
CARNATION
Filed May 14, 1931
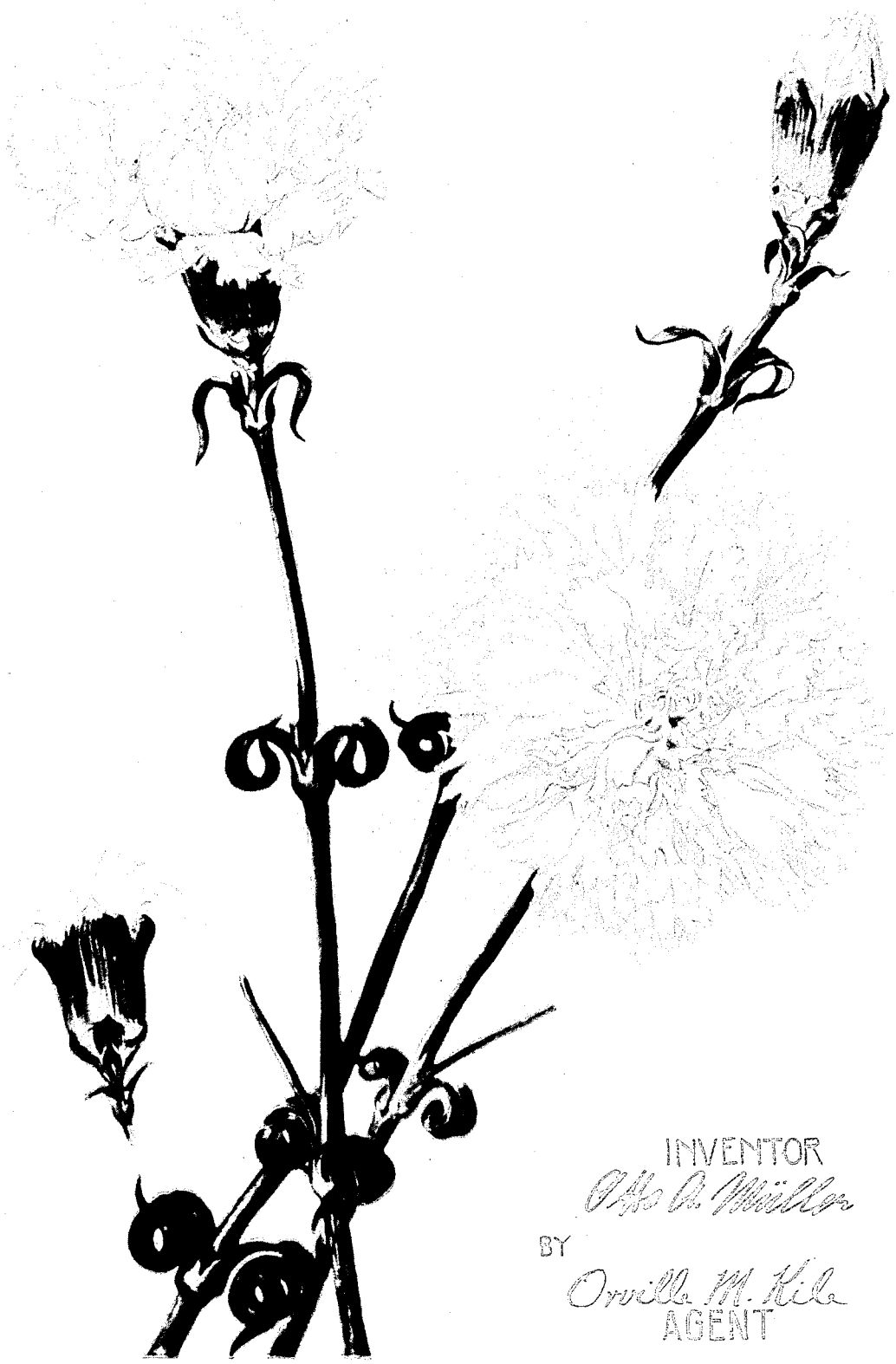
INVENTOR
Otto A. Müller
BY
Orville M. Kile
AGENT Patented Oct. 20, 1931

UNITED STATES PATENT OFFICE

OTTO A. MÜLLER, OF AMBLER, PENNSYLVANIA, ASSIGNOR TO THE FLOREX GARDENS, OF NORTH WALES, PENNSYLVANIA, A CORPORATION OF PENNSYLVANIA

CARNATION

Application filed May 14, 1931. Serial No. 537,455.

My invention relates to improvements in fragrant, white carnations of the type ordinarily known as perpetual blooming or greenhouse forcing carnations. The object of my improvement is to provide a white carnation of the type mentioned having unusually large size, heavy petalage and full, high centers; having a calyx so constructed as to support this type of flower without bursting; having a stiff, unusually long stem capable of supporting such a large and heavy flower; and having superior qualities of productiveness, reproduction and long retention of its fresh appearance when cut, as well as other desirable qualities.

This new carnation was first discovered by me on or about March 1, 1929, as a result of careful and systematic observations made by me for such purpose. This new variety was found as a sport on a plant of pink Sophelia. I immediately took steps to reproduce and develop this new variety and have done so continuously since that time. In constitution, growth and size of bloom as well as in other qualities it greatly surpasses its pink parent Sophelia. This new carnation has not yet been offered for sale.

The accompanying illustrations show in full color and about natural size, a bud, a half opened flower and a fully opened flower of my new carnation.

The following is a detailed description of this new carnation:

An upright, vigorous growing plant 3 to 4 feet in height, a splendid producer and of strong constitution resistant to disease.

Flowers: Pure white to the casual observer but upon close inspection one to five petals in nearly every flower are found to have a slight edging or flecking of pink, also a slightly creamy tint on some of the central petals is noticeable to the artist skilled in analyzing color and shadow values; under ordinary good culture blossoms grow 3½ to 4 inches in diameter, the size being attained partly by unusual length of outside petals and partly by the great number of petals; petals number about 75 to 80 in a normal blossom if all small petals are counted; edges rather deeply and irregularly toothed and partially folded and longitudinally curled so as to give a crinkled appearance, petals are exceedingly numerous and close together in central portion of flower completely filling the center and generally concealing the styles although occasionally the tops of the two curved white styles are visible among the closely set petals. Two styles arise from the seed pod or if considered as a single style it branches into two parts just as it emerges from the seed pod. The flower has a high center making it practically semi-spherical. The petals are of a texture not easily damaged or bruised. Moderately fragrant.

Calyx: The calyx is relatively short and wide at the top, measuring an inch or more across at the top. It consists of a single tube one and one-quarter inches long, made up of five subdivisions or lips separated at the top by moderately deep indentations. This gives a spreading or open mouth effect which aids in preventing bursting of the calyx, an important point due to the extreme fullness of the flower. Each of the five calyx lips is provided with a humped spring-like development which, while tending to hold the flower together in a compact mass, gives the necessary elasticity to prevent the bursting of the calyx cup. The calyx cup is further reinforced by well developed bracts at its base which reach up one third the distance to the top of the calyx cup.

Buds: Relatively short and wide. When half opened the center of the flower has a distinct cream tinge which lessens as the flower opens further and when full blown the creamy tint is scarcely noticeable except to a color artist.

Stems and foliage: Stems are from 36 to 43 inches long, smooth, stiff and amply capable of supporting the heavy flower; deep dark green in color although overcast with a gray bloom, and having rather short blunt leaves, characterized by their tendency to roll or curl extremely and tightly. The last four or five pairs of leaves nearest the flower roll into curls consisting of one to two and one half turns and lie close up to the stem. The fourth pair of leaves below the flower are usually not over 2¼ inches long and about ⅜ inches wide at their widest point.

The more important features which I believe distinguish my new carnation from all other known varieties are:

First; the flower is very large—larger than any other white carnation known to me and larger than most colored carnations.

Second; it has a larger number of petals than any other existing white carnation known to me. When the small petals are all included the number runs 75 to 80. Omitting the smallest petals and comparing with other white varieties on the same basis, the relative counts are as follows:

| | Petals |
|---|---|
| My new variety | 66 |
| Arctic | 57 |
| Senator | 42 |
| White Matchless | 41 |

Third; the flower has a fuller, higher center than most other white varieties, thus giving it a somewhat hemi-spherical appearance, a character much desired by florists.

Fourth; the calyx cup is short and wide and has much more pronounced developments for preventing splitting, than do most other varieties. This is highly important in a carnation as full and heavy as is my new variety. Chief among these improved calyx-cup characters are (*a*) the short, wide-mouthed, stout structure (*b*) the moderately deep, well-formed slits between the lips of the calyx cup (*c*) the unusually large humped, spring-like developments on the lips of the calyx cup which give a high degree of elasticity and prevent bursting.

Fifth; the leaves beginning some four inches below the flower and including the next four or five pairs below, are rolled much more tightly than in any other white variety known to me. These leaves are also relatively short and blunt as compared to most other varieties.

Sixth; flowers cut and placed in water will under ordinary conditions retain their freshness of appearance ten days to two weeks—a period much longer than that of the usual carnation.

Seventh; this variety is an exceptionally easy propagator and makes a noticeably vigorous growth as compared with rooted cuttings of other varieties grown alongside. Other desirable qualities are great length of stem and satisfactory quality of flower production.

I claim:

The carnation as shown and described, characterized particularly by its white blossom slightly flecked with pink, unusually large in size and having a high center; its strongly constructed calyx; its stiff, unusually long stem; and its superior reproductive and keeping qualities.

OTTO A. MÜLLER.